United States Patent
Novak et al.

(10) Patent No.: US 6,436,114 B1
(45) Date of Patent: Aug. 20, 2002

(54) APPARATUS FOR TREATING BODY TISSUE WITH ULTRASOUND

(75) Inventors: Pavel Novak; Rudolf Henes, both of Schaffhausen; Beat Krattiger, Beringen, all of (CH)

(73) Assignee: Storz Endoskop GmbH (CH)

( * ) Notice: Subject to any disclaimer, the term of this patent is extended or adjusted under 35 U.S.C. 154(b) by 0 days.

(21) Appl. No.: 09/634,309

(22) Filed: Aug. 8, 2000

Related U.S. Application Data

(63) Continuation of application No. PCT/EP99/00892, filed on Feb. 11, 1999.

(30) Foreign Application Priority Data

Feb. 18, 1998 (DE) .......................... 198 06 718

(51) Int. Cl.[7] .................................. A61B 17/32
(52) U.S. Cl. ........................ 606/169; 606/170
(58) Field of Search ....................... 606/169, 170, 606/171; 604/22

(56) References Cited

U.S. PATENT DOCUMENTS

| | | | |
|---|---|---|---|
| 4,672,965 A | * 6/1987 | Baum | 604/22 |
| 4,838,853 A | 6/1989 | Parisi | 604/22 |
| 5,047,043 A | 9/1991 | Kubota et al. | 606/169 |
| 5,167,619 A | 12/1992 | Wuchinich | 604/22 |
| 5,176,677 A | 1/1993 | Wuchinich | 606/46 |
| 5,188,102 A | 2/1993 | Idemoto et al. | 128/24 |
| 5,322,055 A | 6/1994 | Davison et al. | 601/2 |
| 5,346,502 A | 9/1994 | Estabrook et al. | 606/169 |
| 5,403,307 A | 4/1995 | Zelman | 606/6 |
| 5,674,235 A | 10/1997 | Parisi | 606/169 |
| 5,906,628 A | * 5/1999 | Miyawaki et al. | 606/169 |
| 6,056,735 A | * 5/2000 | Okada et al. | 606/169 |
| 6,129,735 A | * 10/2000 | Okada et al. | 606/169 |
| 6,139,561 A | * 10/2000 | Shibata et al. | 606/169 |

FOREIGN PATENT DOCUMENTS

| | | |
|---|---|---|
| DE | 40 42 435 C2 | 2/1994 |
| DE | 198 06 718 A1 | 8/1999 |
| EP | 0 238 667 | 9/1987 |
| EP | 0 384 672 | 8/1990 |
| EP | WO93/14708 | 9/1993 |
| EP | 0 591 619 A1 * | 4/1994 |
| EP | 0 695 535 A1 | 8/1995 |
| JP | 08275948 * | 10/1996 |

* cited by examiner

Primary Examiner—Gary Jackson
(74) Attorney, Agent, or Firm—St. Onge Steward Johnston & Reens LLC

(57) ABSTRACT

An apparatus for treating body tissue with ultrasound is provided having a generator and means for transmitting ultrasound to the tissue. The apparatus comprises a hollow probe for suctioning off treated tissue. The hollow probe is provided with a cutting blade in the region of the distal end of the probe and grasping means having a first and a second jaw are provided.

13 Claims, 5 Drawing Sheets

APPARATUS FOR TREATING BODY TISSUE WITH ULTRASOUND

CROSSREFERENCE OF PENDING APPLICATION

This application is a continuation of pending international application PCT/EP99/00892 filed on Feb. 11, 1999 and designating the United States.

BACKGROUND OF THE INVENTION

The invention relates to an apparatus for treating body tissue with ultrasound having a generator and means for transmitting ultrasound into the tissue as well as a hollow probe for removing the treated tissue.

Such an apparatus is described for example in the brochure "SONOTOM 110, Ultraschallaspirator", 9/95, of the company Berchthold GmbH & Co, Medizin-Elektronik, Tuttlingen, Germany.

Ultrasound is not only used for diagnostic purposes for viewing body structures of varying density, it is also used for therapeutic purposes. Ultrasound is either applied externally to the skin or directly within the body at the tissue to be treated by means of corresponding laparoscopic instruments, optionally with endoscopic control.

As a result of the ultrasound treatment, the tissue is heated and caused to denaturate, the so-called (thermo) coagulation. Apart from heat development, ultrasound has a mechanical effect in the form of so-called cavitation. Sound waves propagate in a medium as periodic density fluctuations of the medium. A volume element of the medium is alternately compressed (higher pressure) and expanded (lower pressure). The lower pressure in a liquid, for example in the cytoplasma of the cells or in the tissue fluid can cause vapor bubble formation, which destroys the cells and tissue.

Such an ultrasound treatment is suited for disintegration or dissolution of soft tissue, for example fat tissue. Generally, ultrasound waves in the region of 26 kHz are employed. The coagulated and/or disintegrated tissue is suctioned into a tube-shaped hollow probe, where in addition a washing means for flushing purposes is normally also provided. The flushing fluid is passed through a hollow space between the probe and an outer shaft. The flushing fluid mixed with the cell or tissue residue is suctioned off through the hollow probe.

Such ultrasound treatments are particularly employed for the destruction of tumorous tissue. It is especially applied in liver surgery, because one can skeletonize, i.e. only tissue can be removed from an organ, for example the liver, without cutting or destroying blood vessels of the organ.

However, since ultrasound can only destroy extremely soft tissue in loose cell structures, an ultrasound treatment of more solid tissue and tumors or other hard tissue is not sufficient. Sharper cutting devices, scalpels, etc. are employed which additionally complicates the operation.

Other medical instruments such as surgical knives or scalpels employ ultrasound, which are set into vibration by means of ultrasound. Such an "ultrasound driven" surgical knife for laparoscopic application is disclosed in WO 93/14708. A knife is slidably arranged in the interior of a shaft, from which it is drawn out for the operation. Ultrasound energy is transmitted directly and exclusively to the knife, which is then excited to undergo vibration. A therapeutic application of ultrasound for tissue disintegration is not possible with this surgical cutting device. In addition, it is not possible to remove the cut tissue parts from the operation field. Furthermore, the device is limited to diameters larger than 1 cm.

A further development of this surgical knife is disclosed in U.S. Pat. No. 5,346,502, which is similar in that ultrasound is applied to the surgical knife for vibration. In this case, an outer diameter of the shaft of 5 mm is achieved. This instrument however is extremely complicated in manufacture, because the shaft is made of PTFE and must be subjected to several expansion and contraction processes. In addition, it is not possible to apply ultrasound to destroy soft tissue with this knife.

The German patent DE 40 42 435 C2 discloses an ultrasound treatment apparatus having a hand piece with an ultrasound oscillator and a plurality of probes connectable to the hand piece. Thus an ultrasound apparatus is provided, which is inexpensive with respect to purchase and maintenance costs and at the same time can be used for the most different applications.

The European patent application EP 0 384 672 A2 discloses an ultrasound probe by which the distal suction opening is variable in its form and size to achieve an optimal suction force for withdrawing treated tissue.

The European patent application EP 0 238 667 A1 discloses an ultrasound instrument whose distal end is formed in spoon shape. A central flushing channel supplies fluid to the spoonlike distal end.

The U.S. Pat. No. 5,188,102 describes a surgical knife driven by ultrasound to undergo vibration. A central flushing channel is provided by which a flushing fluid is fed to the distal end, particularly at an angle of 5° to 90° with respect to the cutting plane.

The U.S. Pat. No. 5,047,043 also describes a surgical knife driven by ultrasound, by which an endoscope is inserted to observe the distal end visually.

The European patent application EP 0 695 535 A1 describes a gripping instrument driven by ultrasound, which can grasp the tissue removed by ultrasound.

The U.S. Pat. No. 5,322,055 describes an apparatus driven by ultrasound, which is suitable for cutting and coagulating. A clamping device provided at the distal end, where the tissue to be coagulated is held between a moveable mouth portion and a stationary mouth portion.

In view of the above background art, an object of the present invention is to provide an improved apparatus for therapeutic treatment of body tissue with ultrasound, which apart from removing soft tissue structures also makes it possible to remove harder tissue structures with constructively simple means.

SUMMARY OF THE INVENTION

According to the present invention, an apparatus of the abovementioned type is provided, which has a cutting blade in the region of the distal end of the hollow probe and a grasping means having a first and a second jaw. In conventional ultrasound devices for therapeutic treatment, the hollow probe serves only to draw off and discharge the coagulated and fluidized cell and tissue components, optionally to further inject a flushing fluid into the operation area and to remove it again.

By providing a cutting blade at the distal end of the probe, i.e. at the probe tip which is open for suction purposes, a multifunctional medical instrument is provided in simple manner. The soft tissue components can be disintegrated and suctioned off and at the same time, more rigid tissue portions which are insensitive to ultrasound, can be cut out and also removed. The effect is exploited, that the end of the probe located in the operation area can be excited to undergo vibration, also in therapeutic ultrasound applications. The vibrating cutting blade has excellent cutting properties, even when the blade itself is comparatively blunt.

The function of destroying tissue in the present apparatus is further enhanced by the heat generation of the therapeutic ultrasound waves. Thus it is possible with a single instrument to simultaneously disintegrate tissue through ultrasound, to cut and/or scrape off with the cutting blade and also to coagulate, whereby the continuously loosened cell or tissue pieces are removed from the operation area.

It will be understood that the cutting blade can be used to separate hard or soft tissue components, for example to separate fat tissue from subcutaneous tissue. Under these circumstances, the apparatus of the present invention is used as a cutting and suction apparatus.

The provisions of the grasping means has the advantage that the present apparatus has two further functions, which are often needed in operations where tissue is to be removed. For example, vessels, nerves, etc. can be grasped and such tissue structures can be cut. When cutting arteries, it is advantageous that the heat generation caused by ultrasound also causes coagulation and therefore helps stop the bleeding.

The grasping and cutting function is necessary especially when solid tissue components are to be removed or to be cut and then removed. When the ultrasound is turned off, the present apparatus becomes a pinching or clamping means with the two jaws arranged at the distal end of the probe, with which blood vessels can be held fixed without cutting them.

The present invention thus unifies several functions, which in the mentioned applications are necessary directly in the operation area and it also saves the operator from frequent changes of surgical devices. Such operations are therefore substantially easier and faster to perform as has been previously possible. The multifunctionality of the apparatus is achieved with very simple means, namely by providing the distal end of the hollow probe with a cutting blade and with two jaws for grasping and/or cutting.

In a preferred embodiment, the cutting blade is an integral part of the probe wall. This has the advantage that the blade can be manufactured simply, namely simultaneously with the hollow probe. In addition, high reliability is achieved with this measure, as means for securing the cutting blade to the distal end of the probe are not required.

In a particularly preferred embodiment, the cutting blade is formed as a projection from the probe wall. The cutting blade can be flat or curved, it can be tampered or broadened depending on the desired application.

The formation of the cutting blade as a projection has the considerable advantage that the present apparatus receives an additional function, namely it can also be used as a spattle. The blade, which can be relatively blunt, can then serve as a spattle surface for scraping off tissue when the ultrasound source is turned off. The scraped off tissue is located on the flat projection in a position directly before the opening in the hollow probe and can therefore be directly suctioned off.

When the ultrasound generator is turned on, the projection begins to vibrate and has the effect of a sharp cutting blade. Preferably the cutting blade is exposed and can readily access the tissue to be cut.

In a further embodiment of the present invention, the first jaw of the grasping and cutting means is formed by the cutting blade. This has the advantage of being constructively simple, since only the second jaw needs to be additionally provided at the distal end of the probe.

In a further embodiment, the second jaw of the grasping and/or cutting means is slidable along the longitudinal axis of the probe, consists of a super elastic material and is bent backward of the first jaw in the state of being extended out of the hollow probe. When being drawn into the hollow probe, it moves toward the first jaw.

The shifting of the jaw along the longitudinal axis can be accomplished for example with an actuator element, which is operated from the proximal side of the apparatus. The super-elastic material can be for example Nitinol, a nickel-titanium alloy, which is a so-called "memory material". The material has the property that after being deformed it always returns to its original form. This has the advantage that the grasping and cutting means is simple in manufacture and in operation, without the necessity of joints, pivots or the like. The curvature of the second, slidable jaw can be oval or flattened or can also comprise complicated bendings or curvatures, depending on the desired application.

In a further embodiment of the present invention, a guide and glide element for the second jaw is provided in the interior of the hollow probe. This has the advantage that the sliding of the jaw and therefore the opening and closing of the jaw for releasing or gripping is performed without friction. The guide and glide element is preferably made of Teflon. This has the further advantage that a possible welding of the second jaw to the probe, which under some circumstances could occur when the ultrasound is activated and generates heat, is reliably avoided.

In a further preferred embodiment, the second jaw of the grasping and cutting means is spread apart from the first jaw by pivotal movement. By pivoting about a transverse axis, the second jaw is thus spread apart from the first jaw in an open position of the grasping and/or cutting means or it is flapped shut again in the direction of the first jaw. It is also possible to turn the second jaw completely back from the distal opening of the probe, so that it does not interfere with the cutting function with the cutting blade or with the suctioning off of tissue residue.

In a further preferred embodiment of the present invention, the probe comprises an outer shaft in which the second jaw is pivotally secured. This has the advantage that the outer shaft can be used for securing or journaling the second jaw. The pivot action can be achieved for example with a rod or cable, which can also be provided within the outer shaft wall. Alternatively, the second jaw can be journaled such that a shifting of the outer shaft causes the rotation of the second jaw. In addition, the outer shaft advantageously protects the hollow probe from mechanical loads.

A flushing fluid is supplied. in the space between the outer shaft and the hollow probe. By providing the outer shaft, it is also possible to withdraw the cutting blade entirely into the shaft, whereby undesired tissue damage is avoided, for example when introducing the probe into the body.

In a further embodiment of the present invention, the outer shaft comprises an upper half and a lower half, which are shiftable relative to one another at a separation line along the longitudinal axis of the probe. A shifting of the half on which the second jaw is anchored causes a pivotal movement of the second jaw. This has the advantage that the relative shifting of the outer shaft halves exerts the necessary tension on the second jaw to rotate it relative to the first jaw.

In a further preferred embodiment of the present invention, the grasping and/or cutting means comprises a tube having a projection and being disposed in the interior of the hollow probe. The probe and the tube are rotatable relative to one another and the projection interacts with the cutting blade of the probe. This has the advantage that the apparatus is formed as a rotary pincher or forceps. By rotating the probe and the inner tube relative to one another either by rotating the inner tube or the outer tube or both tubes together, tissue sections can be brought between the projection and the cutting blade and either be grasped or even be cut, so that the device can act as rotary grasping forceps or as rotary cutting forceps.

With this geometry, a particularly slender structure is formed so that no jaws or tongs which extend to the side beyond the circumference of the outer shaft are present. This embodiment is particularly.employed when relatively small pieces are to be grasped or cut.

In a further embodiment of the present invention, the projection of the inner tube is placed in a rotary position to lie closely adjacent to the cutting blade, so that both projections act as a compact element. This has the advantage that in this rotary position one can work with the probe as if no grasping means were present, since the two tubes are rotated with respect to one another so that their projections work as one structure. In this angular position, this compact structure can be used either as a cutting blade and/or as a spattle.

In a further embodiment, the axial edges of the projections are blunt. This has the advantage that the pincher or forceps are designed to perform only grasping and cutting does not take place.

In a further embodiment of the invention, the axial edges of the projections are sharp. In this embodiment, the apparatus is designed to work as a cutting forceps. It is also possible that both embodiments be combined, i.e. a sharp edge and a blunt edge are formed, so that in one rotation direction a grasping effect is achieved and in the other rotational direction a cutting effect is achieved.

In a further embodiment, the hollow probe can be supplied with high frequency current (HF). This allows a further function of the present apparatus, namely its use for HF coagulation, for example to rapidly and efficiently close off strongly bleeding vessels by applying HF current. It will be understood that a high frequency generator will be necessary to produce the HF power. The HF power is transmitted through the probe to the proximal cutting blade and causes a denaturation of the tissue contacting the cutting blade.

It will be understood that the above-mentioned features and those to be discussed below are not only applicable in the given combinations, but may be present in other combinations or taken alone without departing from the scope of the present invention.

BRIEF DESCRIPTION OF DRAWINGS

Preferred embodiments of the present apparatus will be discussed in more detail below with reference to the drawings.

DETAILED DESCRIPTION OF PREFERRED EMBODIMENTS

Figure 1:
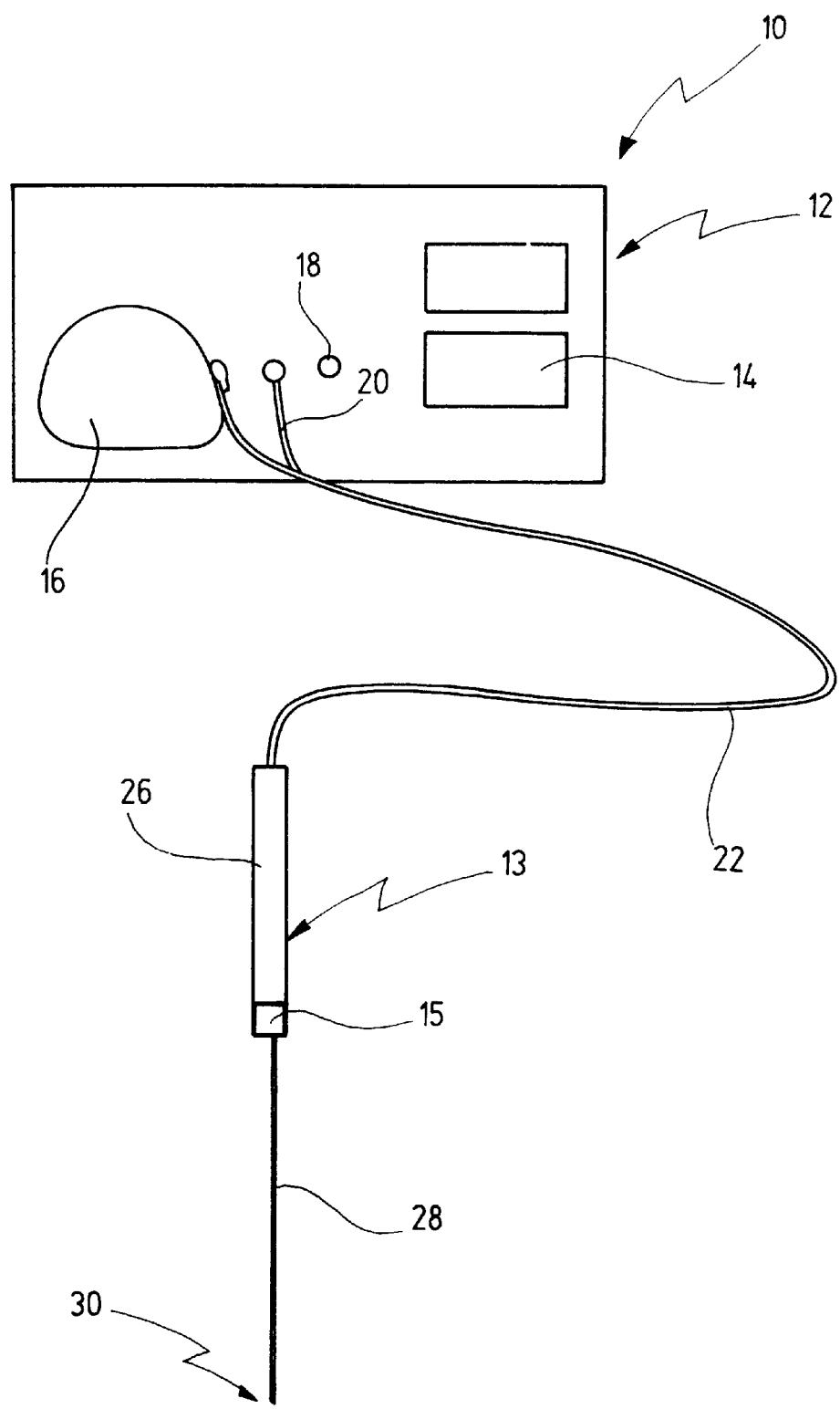
FIG. 1 shows a schematic representation of an apparatus according to the present invention for treatment of body tissue with ultrasound.

An apparatus for treating body tissue with ultrasound is shown in FIG. 1 and generally designated with the numeral 10. The apparatus 10 comprises a generator 12 and means 13 for transmitting ultrasound to the body. The means 13 include an ultrasound transducer 15 which generates ultrasound.

The generator 12 comprises two display fields 14, a peristaltic pump 16 and terminal jacks 18. A supply line 20 is fed through a flexible tube 22 which comes from the pump 16. The tube 22 and the supply line 20 are connected to a handle 26 and end in a hollow probe 28. The hollow probe 28 has a distal end 30, whose configuration is better seen in FIGS. 2 to 4.

A flushing medium is supplied between an outer shaft (not shown) and the probe 28 to the distal end 30. The probe 28 includes a channel 32 for suctioning off fluid and tissue components or pieces. The wall 34 of the probe ends in a flat surface projection 36, whose edges 38 act as cutting edges. It therefore acts as a cutting blade 39.

In use of the apparatus 10, ultrasound is generated by the transducer 15, for example 24 kHz, is transmitted to the distal end 30 of the probe 28. The transmitted ultrasound particularly disintegrates soft tissue, however not hard tissue, and fluidizes same. In addition, the heat development produced by the ultrasound leads to coagulation of the tissue. At the same time, the ultrasound fed to the probe 28 causes a vibration of the distal end 30. This vibration activates the blade 39 which then efficiently and rapidly cuts through tissue, also hard tissue. Cut and loosened pieces of tissue are directly drawn through the channel 32 and through the tube 22 connected to the pump 16.

Figure 2:
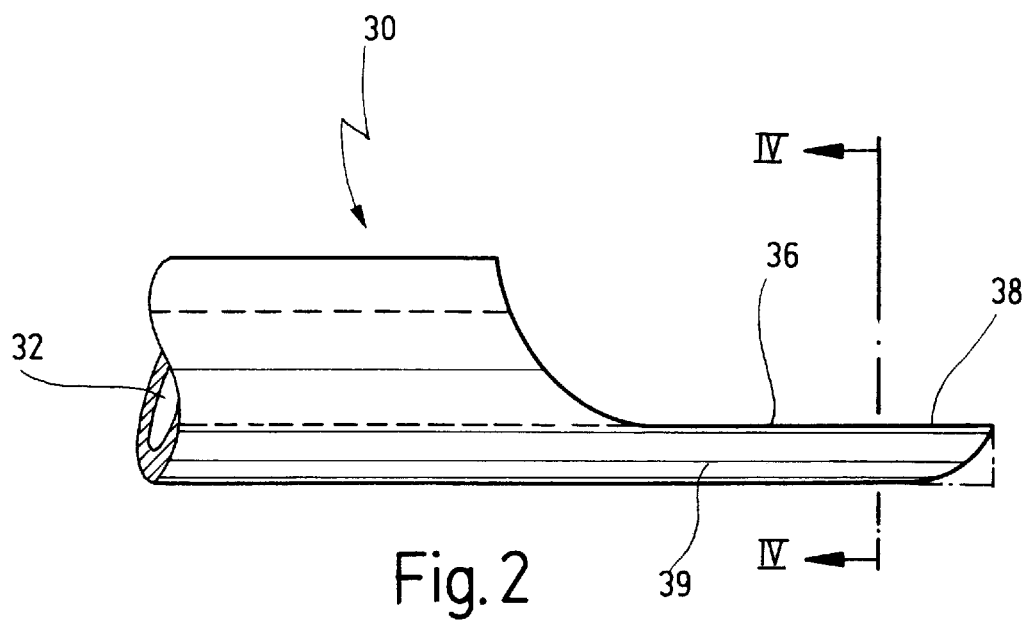
FIG. 2 shows a highly enlarged side view of the distal end of a first embodiment of a hollow probe according to the apparatus of the present invention, with grasping means not yet mounted.
Figure 3:
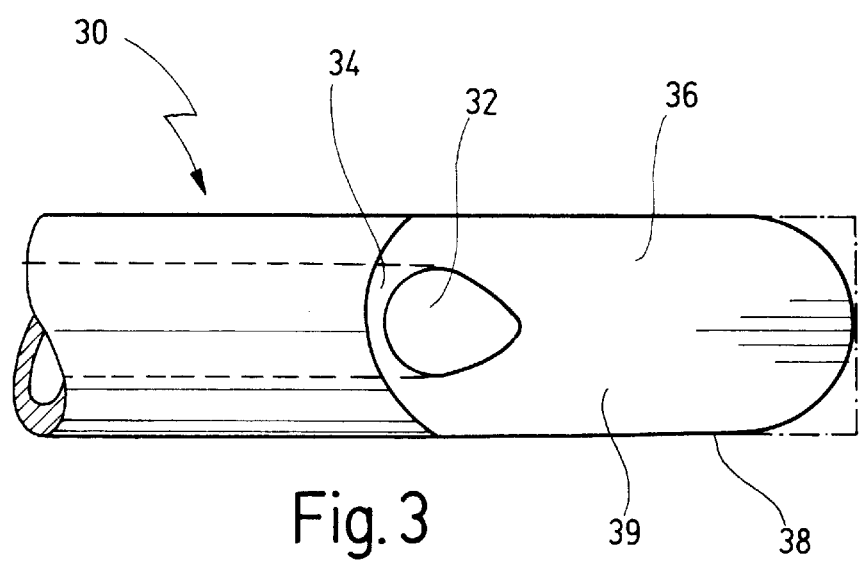
FIG. 3 is a plan view of the distal end of the probe of FIG. 2.
Figure 4:
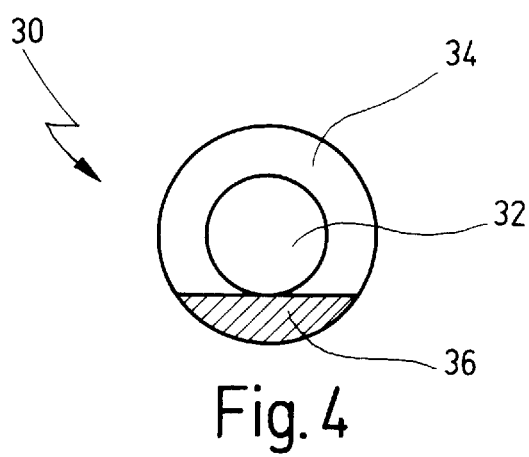
FIG. 4 shows a cross-section along the line IV—IV of FIG. 2.
Figure 5:
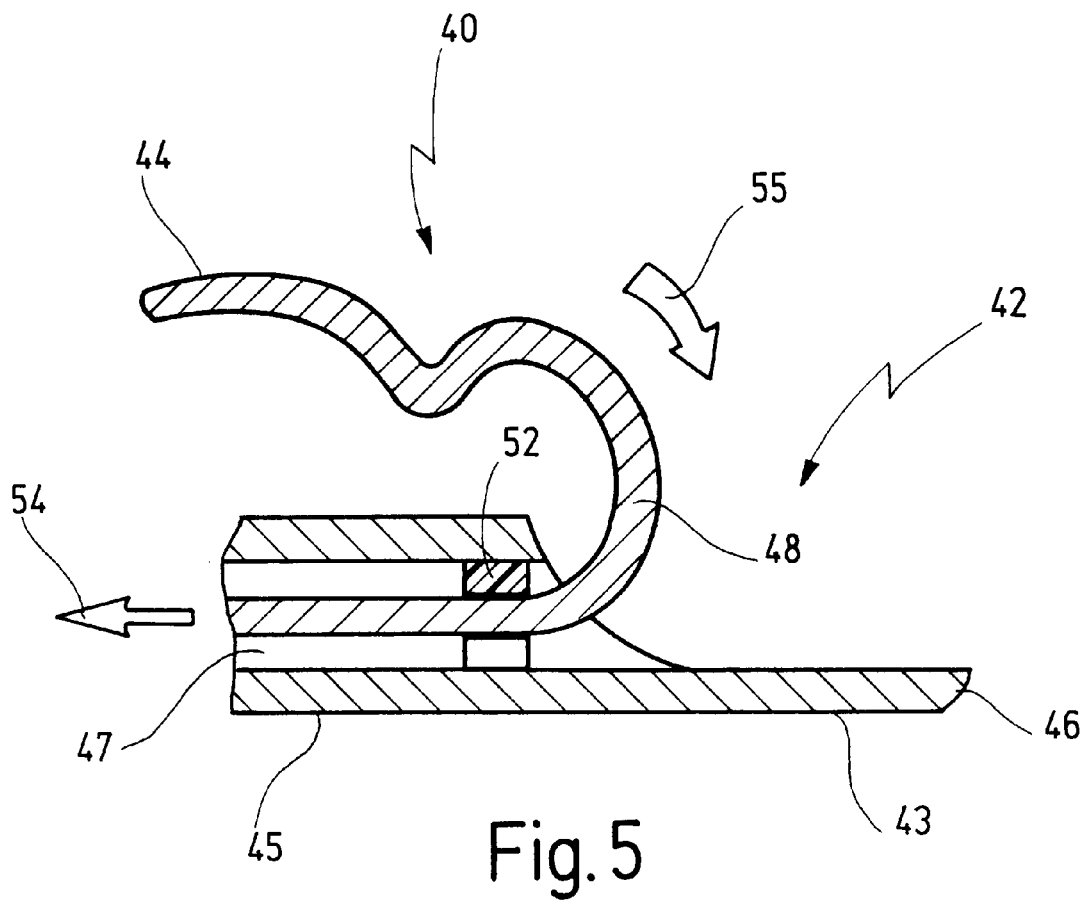
FIG. 5 shows a cross-section of the distal end of the probe with means for grasping, namely in an open position of the grasping means.
Figure 6:
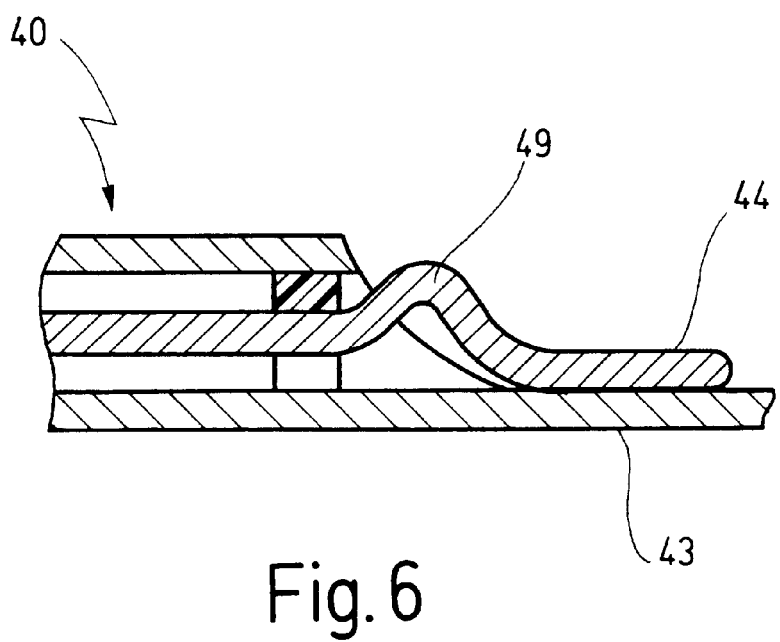
FIG. 6 shows a cross-section corresponding to FIG. 5 however in the closed position of the grasping means.

In the embodiment shown in FIGS. 2 and 3, the blade 39 has a rounded, sharp end edge. The edge could also be cornered and blunt as shown by the dot-dashed line. FIGS. 5 and 6 show the completely assembled probe together with the grasping means. Only the distal end of the probe is shown, which is generally designated with the numeral 40. The distal end 40 comprises grasping means 42, which consist of a first jaw 43 and a second jaw 44.

The first jaw 43 is a projection of the probe wall 45 and comprises a cutting blade 46. A second jaw 44 is shiftably arranged in a lumen 47 of the probe, which is made of a superelastic material with shape memory, a so-called memory metal. The memory metal is preferably a nickel-titanium alloy. It extends out of the lumen of the probe. The second jaw 44 is guided in the lumen 47 by a guide and glide. element 52 made of Teflon.

FIG. 5 shows an opened position of the grasping means 42. The second jaw is extended far out of the lumen 47 and bends outwardly and backwardly due to the memory effect to form a protuberance 48, where it extends to lie outward of the proximal end 40. By shifting the second jaw 44 back into the lumen 47 in the direction of the arrow 54, the second jaw 44 bends and folds forwardly in the direction of the arrow 55. By further shifting in the direction of the arrow 54, the second jaw 44 comes to rest on the first jaw 43. This position shown in FIG. 6 is the closed position or the grasping position of the grasping means 42. In this position, tissue layers, arteries or nerves can be grasped and held fixed.

A hump 49 of the second jaw forms a stop so that complete insertion of the second jaw into the probe lumen 47 is prevented. The hump 49 engages the probe wall and is caught, whereby the resistance force is enhanced.

Figure 7:
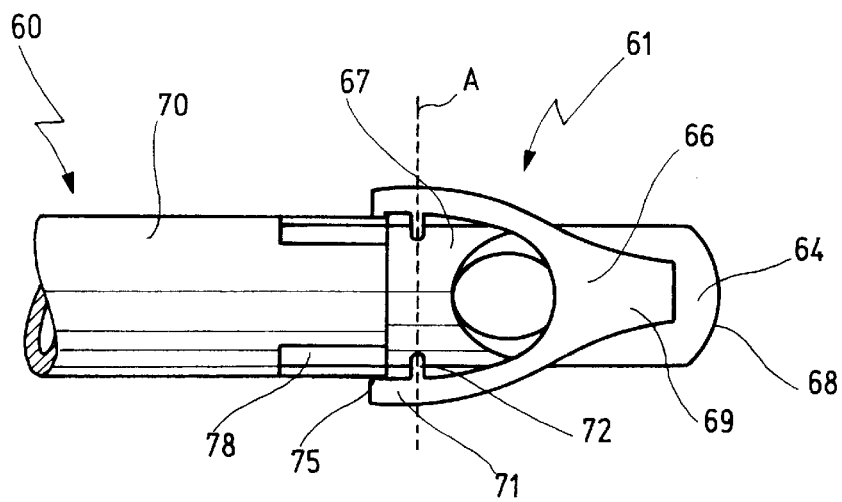
FIG. 7 shows a plan view of the distal end of a further embodiment of the probe of the apparatus of the present invention with a grasping means in a closed position and with an outer shaft.
Figure 8:
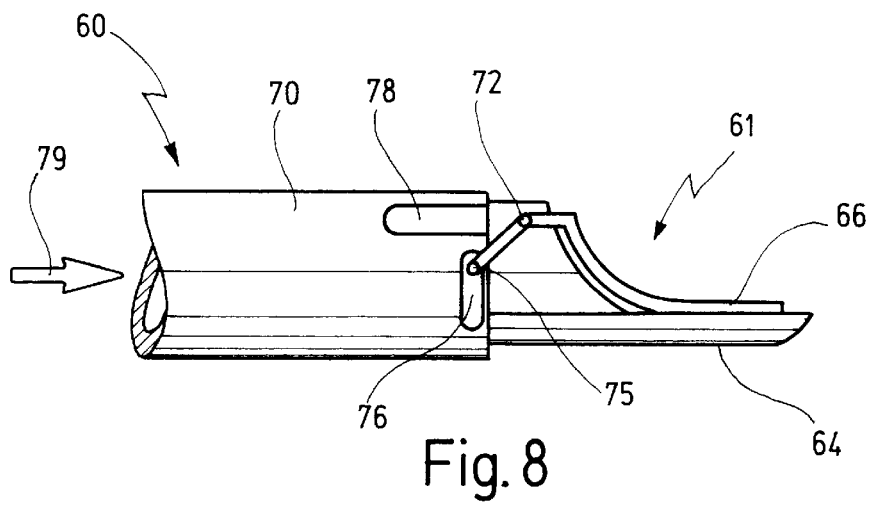
FIG. 8 shows a side view of the distal end corresponding to FIG. 7, namely in the closed position of the grasping means.
Figure 9:
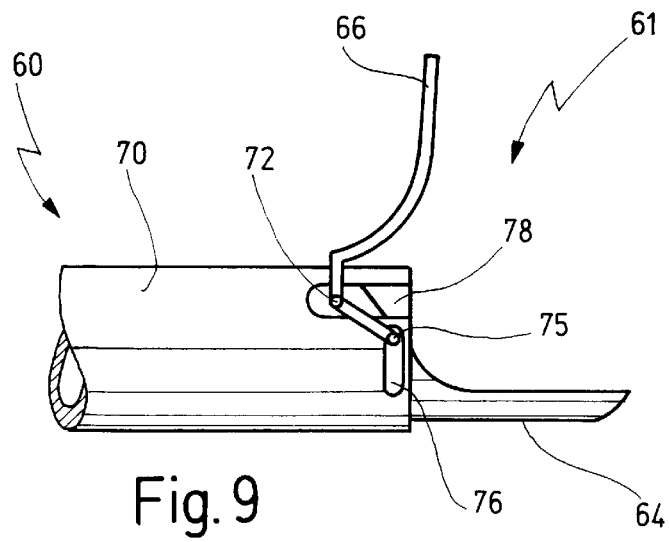
FIG. 9 shows a side view corresponding to FIG. 8, however in the open position of the grasping means.
Figure 10:
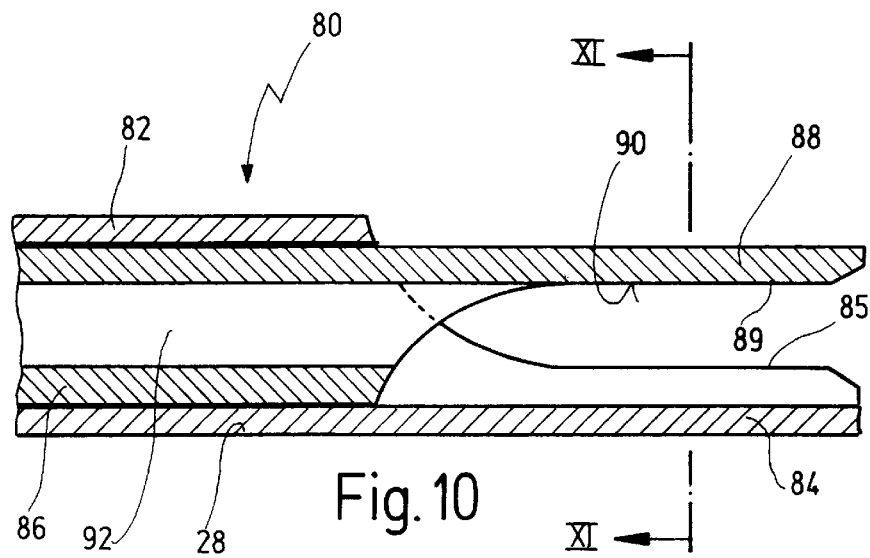
FIG. 10 is a longitudinal cross-section of a further embodiment of the distal end of a probe, which is formed as a rotary pincher.

A further embodiment of the probe with grasping means is shown in FIGS. 7 to 9. A distal end of a probe is generally indicated with numeral 60. Grasping means 61 are provided at the distal end 60, which consists of a first jaw 64 and a second jaw 66. The first jaw 64 comprises a projection of the probe wall 67 and includes a cutting blade 68.

The second jaw 66 comprises a tongue 69 from which two bows 71 extend proximally. The bows engage about the probe wall 67 as well as the outer shaft 70 in which the distal end 60 is axially slidable.

The bows 71 are secured by means of pin 72 to be pivotal in corresponding receptors of the probe wall 67. In addition, the bows 71 at their ends comprise radially inwardly extending pegs 75, which are slidably engaged in slot 76 of the outer shaft 70. The wall of the outer shaft 70 also is provided with recesses 78 which extend along the longitudinal axis in the upper one third of the outer shaft 70.

In the closed position of the grasping means 61 shown in FIGS. 7 and 8, the tongue 79 of the second jaw 66 lies flat on the first jaw 64. The outer shaft 70 is shifted to its maximal distal position. By means of the peg 75 engaging the slot 76, a pressure is applied to the second jaw 66, so that a grasping or holding of tissue pieces, vessels, etc. is possible in this position.

By pushing the outer shaft 70 in the direction of the arrow 80, the grasping means 71 goes over to a position open by 90° as shown in FIG. 9. The pegs 75 move in the slot 76 and the second jaw 66 rotates upwardly about its pivot axis A, which is defined by the pin 72. The pin 72 then enters the recess 78.

In the position shown in FIG. 9, the second jaw 66 is rotated upwardly by 90° and opens up the suction channel so that suctioning and flushing can be performed without problem.

With a corresponding design of the geometry, the second jaw 66 can also be rotated by 180°, so that it then would lie in close relationship to the outside of the outer shaft. The second jaw 66 can remain in this position in case no grasping function is desired or needed for a certain time.

In a further embodiment shown in FIGS. 10 to 14, the hollow probe 28 is provided at its outer end with a projection 84. The projection 84 is formed in that a portion of the tube wall is removed at the distal end 80, so that only a defined circumferential section of the tube wall remains, as shown in particular in the cross-section of FIG. 11.

An inner tube 86 is placed in the hollow probe 28, whose outer diameter corresponds to about the clearance inner diameter of the probe 28. The inner tube also comprises a projection 88 at its distal end, which is formed in that a portion of the tube wall is removed.

Figure 11:
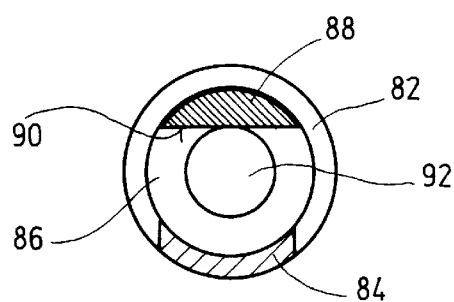
FIG. 11 shows a cross-section along the line XI—XI of FIG. 10, where the projections are illustrated in diametrically opposite positions.
Figure 12:
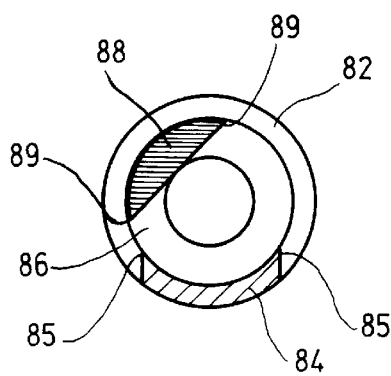
FIG. 12 shows a comparable cross-section as in FIG. 11, where the projection of the inner tube is rotated counter-clockwise by about 45°.
Figure 13:
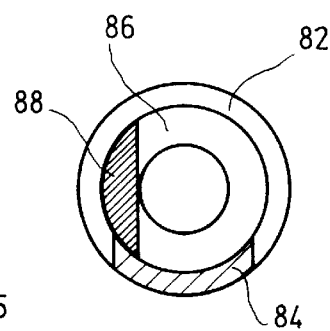
FIG. 13 shows cross-sections similar to FIGS. 11 and 12, where the projection of the inner tube is rotated counter-clockwise by about 90°.

In contrast to the projection 84, the projection 88 is cut so as to provide a flat inner surface 90, as is best seen in the cross-sectional illustration of FIG. 11. The hollow inner space of the inner tube 86 forms a channel 92 for the purpose of suction. In the rotational position of FIGS. 10 and 11, the projection 84 is diametrically opposed to the projection 88 in the inner tube 86. In this position, the hollow probe 28 can be operated as an ultrasound aspirator.

The inner tube 86 is rotatable relative to the tube 82, as the sequence of FIGS. 11 to 14 show. As illustrated in the embodiments, the projection 84 has sharp side edges 85, while the projection 88 has sharp side edges 89. When the inner tube 86 is rotated as in the sequence of FIGS. 11 to 14, a piece of tissue caught between the approaching edges 89 and 85 will be cut off, so that the two projections 84 and 88 perform a cutting operation.

If these edges are blunt, they can act as part of a rotary grasping pincher or forceps.

Figure 14:
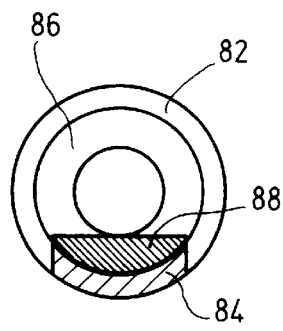
FIG. 14 shows a representation similar to FIGS. 11 to 13, where the projection of the inner tube is rotated by 180° compared to the illustration in FIG. 11 and is closely adjacent to the cutting blade of the probe.

As can be seen in FIG. 14, the two projections 84 and 89 lie closely upon one another and form a compact structure. Their geometry and cross-section correspond approximately to the projection 36 shown in FIG. 4, so that these two portions can act as a spattle. This shows particularly distinctly the flexibility and the multifunctionality of this embodiment.

What is claimed is:

1. An apparatus for treating a body tissue with ultrasound, comprising:
    a generator for generating ultrasound,
    means for transmitting said ultrasound generated by said generator to a body tissue, said means comprising
    a hollow probe for suctioning off a treated tissue resulting from a treatment of said body tissue with said ultrasound,
    a cutting blade provided at a distal end section of said hollow probe, said cutting blade projecting from said distal end of said hollow probe, and
    grasping means provided at said distal end of said hollow probe, said grasping means having a first and a second jaw, said first saw of said grasping means being formed by said cutting blade.

2. The apparatus of claim 1, wherein said jaws of said grasping means are designed to perform a cutting action when grasping a body tissue.

3. The apparatus of claim 1, wherein said cutting blade is an intergral part of said hollow probe.

4. The apparatus of claim 1, wherein said cutting blade is designed as a projection of a wall of said hollow probe.

5. The apparatus of claim 1, wherein said jaws of said grasping means is shiftable along a longitudinal axis of said hollow probe, the second jaw is made of a super-elastic material, the second jaw is bent away from said first jaw in a position being pushed out of said hollow probe, and wherein said bent away second jaw is moved towards said first jaw when said second jaw is drawn into said hollow probe along said longitudinal axis.

6. The apparatus of claim 5, wherein a guide element is provided in an interior of said hollow probe at a distal end section of said hollow probe, said guide element serves for guiding said second shiftable jaw when shifting along said hollow probe.

7. The apparatus of claim 1, wherein said second jaw of said grasping means can be spread apart from said first jaw by a rotational movement of said second jaw about a rotation axis perpendicular to a longitudinal axis of said hollow probe.

8. The apparatus of claim 7, wherein said hollow probe comprises an outer shaft, upon which outer shaft said second jaw is mounted pivotally.

9. The apparatus of claim 8, wherein said outer shaft is movable relative to said hollow probe, a movement of said outer shafts causes a pivotally movement of said second jaw.

10. The apparatus of claim 1, wherein said grasping means comprises a tube having a projection, said tube is received within an interior of said hollow probe, said hollow probe and said inner tube are rotatable relative to one another about a longitudinally axis of said tube, thereby said projection of said tube interacts with said cutting blade of said hollow probe in the sense of two jaws.

11. The apparatus of claim 10, wherein said projection of said inner tube is turnable into an angular position super positing said cutting blade of said probe resulting in a compact structure of said two closely adjacent arranged jaw members.

12. The apparatus of claim 11, wherein side edges of said projection of said inner tube are formed to be sharp edges.

13. The apparatus of claim 1, wherein said hollow probe side has a connector for connecting said hollow probe to a high frequency current.

* * * * *